United States Patent [19]

Diamond

[11] Patent Number: 5,597,697
[45] Date of Patent: Jan. 28, 1997

[54] SCREENING ASSAY FOR INHIBITORS AND ACTIVATORS OF RNA AND DNA-DEPENDENT NUCLEIC ACID POLYMERASES

[76] Inventor: Paul Diamond, 693 Somerville Ave., Apt. 4, Somerville, Mass. 02143

[21] Appl. No.: 315,987

[22] Filed: Sep. 30, 1994

[51] Int. Cl.$^6$ .............................. C12Q 1/68; C12Q 1/48; C12Q 1/02; G01N 21/78
[52] U.S. Cl. .................................. 435/6; 435/4; 435/15; 435/29; 435/193; 436/164
[58] Field of Search ........................... 435/4, 6, 15, 193, 435/29; 436/164

[56] References Cited

U.S. PATENT DOCUMENTS

| | | | |
|---|---|---|---|
| 4,786,600 | 11/1988 | Kramer | 435/320.1 |
| 4,876,197 | 10/1989 | Burke | 435/172.3 |
| 4,880,734 | 11/1989 | Burke | 435/69.1 |
| 4,912,046 | 3/1990 | Henner | 435/252.3 |
| 4,957,858 | 9/1990 | Chu | 435/6 |
| 4,980,281 | 12/1990 | Housey | 435/29 |
| 4,994,368 | 2/1991 | Goodman | 435/6 |
| 5,070,010 | 12/1991 | Hsu | 435/6 |
| 5,079,143 | 1/1992 | Klein | 435/29 |
| 5,112,734 | 5/1992 | Kramer | 435/6 |
| 5,166,057 | 11/1992 | Palese | 435/69.1 |
| 5,194,370 | 3/1993 | Berninger | 435/6 |
| 5,215,899 | 6/1993 | Dattagupta | 435/6 |
| 5,266,464 | 11/1993 | Housey | 435/29 |
| 5,334,525 | 8/1994 | Seeger | 435/194 |

OTHER PUBLICATIONS

Ruet et al. "A Specific Assay for Yeast RNA Polymerases in Crude Cell Extracts" Eur. J. Biochem 90:325–330 1978.
Helgestrand et al. "Antiviral Screening Based Upon Cell–Free Polymerase Models and a New Selective Inhibitor" Proc. 10th Int Cong. Chemother. vol. 1 329–330 1978.
USB Catalog "GeneScribe" 127–132 1990.
Sethi "Comparison of Inhibition of Reverse Transcriptase & Antileukemic Activities Exhibited by Protoberberine & Benzophenonthridine Alcohols & Structure–Activity Relationships" Phytochem. 24(3) 447–454 1985.
Kim B. and Loeb L. A. (1995) Human Immunodeficiency Virus Reverse Transcriptase Substitutes for DNA Polymerase 1 in *Escherichia coli.*, Proc. Nat Acad. Sci–USA 1995, Jan. 1 92(3):684–8.
Spedding G. et al (1994) A Nonradioactive Assay System for Screening for Inhibitors of Reverse Transcriptase Trends in Genetics (10) 11:388–389 Nov. 1994.
Goff et al (1981) Isolation and properties of Moloney murine leukemia virus mutants: use of a rapid assay for release of virion reverse transcriptase, *Journal of Virology*, 38, 239–248 Aug. 1992.
Huang et al (1990) Selective action of 3'–Azido–3'–deoxythymidine 5'–Triphosphate on viral reverse transcriptase and human DNA polymerases, *The Journal of Biological Chemistry*, 265, 11914–11918 Jul. 1990.

Orr et al (1992) DNA chain termination activity and inhibition of human immunodeficiency virus reverse transcriptase by carbocyclic 2', 3'–dihydro–2', 3'–dideoxyguanosine triphosphate, *The Journal of Biological Chemistry*, 267, 4177–4182 Feb. 1992.
Murray and Crocket, "Antisense Techniques: An Overview" in Antisense RNA and DNA, J. A. H. Murray, ed., Wiley–Liss Inc., 1–49 (1992).
Weiss et al. (1992) Synthetic human tRNA$^{Lys3}$ and natural bovine tRNA$^{Lys3}$ interact with HIV–1 reverse transcriptase and serve as specific primers for retroviral cDNA synthesis, *Gene*, 111, 183–197 Feb. 1992.
Wang and Seeger (1992) The reverse transcriptase of Hepatitis B Virus acts as a protein primer for viral DNA synthesis, *Cell*, 71, 663–670 Nov., 1992.
Gossen and Bujard (1992) Tight control of gene expression by tetracycline–responsive promoters, *Proc. Natl. Acad. Sci. USA*, 89, 5547–5551 Jun. 1992.
Kohlstaedt and Steitz (1992) Reverse transcriptase of human immunodeficiencey virus can use either human tRNA3$^{Lys}$ or *Escherichia coli* tRNA2$^{Gln}$ as a primer in an in vitro primer–utilization assay, *Proc. Natl. Acad. Sci. USA* 89, 9652–9656 Oct. 1992.
Parvin and Sharp (1993) DNA topology and a minimal set of basal factors for transcription by RNA Polymerase II, *Cell* 73, 533–540 May 1993.

*Primary Examiner*—Mindy Fleisher
*Assistant Examiner*—Nancy J. Degen

[57] ABSTRACT

The invention provides methods for the identification and discovery of agents which are inhibitors and activators of RNA and DNA-dependent nucleic acid polymerases. The essential feature of the invention is the incorporation of a functional polymerase binding site sequence (PBS) into a nucleic acid molecule which is chosen for its ability to confer a discernible characteristic via its sequence specific activity such that the incorporation of the PBS renders the nucleic acid molecule a functional template for a predetermined RNA or DNA-template directed nucleic acid polymerase (1). In the presence of the polymerase, suitable primer molecules, and any necessary accessory molecules, catalytic extension of the strand of nucleic acids complementary to the template occurs, resulting in a partial or total elimination of (or increase in) the characteristic conferring activity of the reporter-template molecule described due to the antisense effects of the complementary strand or other polymerase-mediated effects. Candidate inhibitors and activators are evaluated for their specific effects on polymerase function, versus polymerase-unrelated effects on reporter-template function, by comparing their ability to decrease or increase the extent of the characteristic conferred by the activity of the reporter-template molecule in the assay to their ability to do so in the control situation in which the activity of the polymerase has been eliminated from the assay. A novel method for controlling gene expression and, in general, the activity of a nucleic acid molecule is also disclosed.

26 Claims, 2 Drawing Sheets

SCREENING ASSAY FOR INHIBITORS AND ACTIVATORS OF RNA AND DNA-DEPENDENT NUCLEIC ACID POLYMERASES

FIELD OF THE INVENTION

The invention relates to a method for identifying agents which inhibit or activate RNA and DNA-dependent nucleic acid polymerases. The invention also relates to a method for controlling the expression of and, in general, the activity of a nucleic acid molecule.

BACKGROUND OF THE INVENTION

The group of DNA-dependent nucleic acid polymerases is comprised of two subclasses of enzymes as follows; 1) the DNA-dependent DNA polymerases which are usually responsible for the replication of DNA genomes and 2) the DNA-dependent RNA polymerases. These polymerases play an essential role in the life cycle of all cells and many viruses. Agents that specifically inhibit the DNA and RNA polymerases of pathogenic organisms are potentially of therapeutic value in the treatment of disease. Inhibitors and activators of DNA-dependent RNA polymerases may also be useful as regulators of gene expression for purposes such as gene therapy. Current assays for inhibitors of DNA-dependent nucleic acid polymerases of the primer extension type work by measuring the effect of an agent on the amount of labeled nucleotide incorporated into a newly synthesized strand by extension of a primer on a DNA template. For a description of the primer extension method see Goff et al, Journal of Virology, 38, 239–248 (1981), Huang et al, The Journal of Biological Chemistry, 265, 11914–11918 (1990), and Orr et al, The Journal of Biological Chemistry, 267, 4177–4182 (1992). Assays for inhibitors and activators of DNA-dependent RNA polymerases may also be based on another method known in the field. Here, by placing under control of a relevant promoter, a gene coding for a protein which confers a discernible characteristic, candidate effectors of the polymerase are evaluated by their effect on the expression of this characteristic. The present invention also utilizes an operable linkage between the activity of a polymerase and the expression of a discernible characteristic, however, the mechanism employed by the present invention is unique and applicable to all classes of RNA and DNA-dependent nucleic acid polymerases.

The group of RNA-directed nucleic acid polymerases is comprised of two subclasses of enzymes as follows: 1) the RNA-dependent DNA polymerases (also referred to as the reverse transcriptases) and 2) the RNA-dependent RNA polymerases. These polymerases play an essential role in the life cycle of many vital pathogens. Two examples of human vital pathogens with an essential requirement for reverse transcriptase activity are Human Immunodeficiency Virus (HIV) and the Hepatitis B Viruses (HBV). Some examples of human viral pathogens with an essential requirement for RNA-dependent RNA polymerase activity are Polio myelitis virus, Human Reovirus, the Influenza viruses, and the Rhinoviruses. The reactions catalyzed by these polymerases are not known to occur in normal human cells and thus they are vital specific and considered good targets for therapeutic intervention by drug therapy. Screening assays which can rapidly and accurately detect the inhibitory activity of various agents toward specific RNA-dependent nucleic acid polymerases can therefore be very useful in the identification of new drug leads.

Much current attention is focused on the identification of inhibitors of the reverse transcriptase of HIV (HIV-RT). The target specific assay type in use is an in vitro primer extension assay in which the ability of an agent to inhibit reverse transcription is determined by comparing the amount of radiolabeled (or otherwise labeled) nucleotide incorporated into a reverse transcribed strand in the presence of the agent being tested versus that incorporated under the same conditions but in the absence of the agent. The RT used in the assay can be a purified product or lysates of HIV-infected cells may be used in which case the agent to be tested may be added to the cells before or after lysis. This assay can be automated for large scale screening but still contains multiple steps including the separation of the incorporated and unincorporated labeled nucleotides. Note that HIV-RT is also a DNA-dependent DNA polymerase.

RNA-template directed nucleic acid polymerases also play a vital role in viral pathogenesis in non-mammalian organisms including plants and in the normal biological function of various non-mammalian organisms including plants. Examples of the former case are various plant viruses with an essential requirement for RNA-dependent RNA polymerase function. An example of the latter case is the normal amplification of RNA by RNA-dependent RNA polymerases in plants. It is anticipated that inhibitors and activators of these polymerases will have uses in the fields of agriculture, biological control, gene control, and gene therapy.

The present invention provides a method for screening agents for their effect on the activity of specific RNA or DNA-dependent nucleic acid polymerases by operably linking the activity of such polymerases to novel template sequences which confer discernible characteristics. The present invention allows for rapid large scale screening of compounds by automation and both large and small scale screening by laboratories or individuals. The present invention also allows for the facile screening of agents and extracts in the non-laboratory field setting and is highly portable. The present invention drastically reduces the number of steps involved in the performance of an assay procedure compared to the primer extension assay method and can utilize a single assay reaction chamber throughout its implementation.

The present invention allows the direct colorimetric determination of the assay results. The assay method of the present invention can be wholly cell-based or comprise a simple in vitro assay system. The present invention makes no use of, nor does it generate, infectious viral particles or other pathogens.

The present invention also provides a novel method for controlling the expression of and, in general, the activity of a nucleic acid molecule. The ability to control the expression of exogenous genes is desirable for the application of gene therapy and for other purposes. One method, as described in Gossen and Bujard, Proc. Natl. Acad. Sci. USA, 89, 5547–5551 (1992), allows differential control of the expression of individual genes in mammalian cells in response to tetracycline by utilizing regulatory elements of the Tn10-specified tetracycline resistance operon of E. coli. Other methods described in the literature for eukaryotic gene control utilize various inducible promoters responsive to, for example, heavy metal ions, heat shock, and hormones. The present invention provides not only a method for controlling the expression of genes but also a method for controlling the activity of catalytic RNA and DNA molecules and other nucleic acid molecules.

The present invention utilizes the effects of antisense RNA and DNA on a complementary nucleic acid molecule.

For a review on the subject, see Murray and Crocket, "Antisense Techniques: An Overview" in Antisense RNA and DNA, J. A. H. Murray, ed., Wiley-Liss Inc., 1–49 (1992). The present invention also utilizes the interaction between a polymerase and its respective polymerase binding site in a template molecule. The polymerase binding site and primer requirements for HIV-RT are disclosed in Weiss et al, Gene, 111, 183–197 (1992) and Kohlstaedt and Steitz, *Proc. Natl. Acad. Sci. USA* 89, 9652–9656 (1992). Those for HBV-RT are disclosed in Wang and Seeger, *Cell,* 71, 663–670 (1992).

Further objects and advantages of this invention will become apparent from a consideration of the drawings and ensuing description.

SUMMARY OF THE INVENTION

Figure 1:
FIG. 1 illustrates a functional polymerase binding site sequence (PBS) incorporated into an RNA molecule which confers a discernible characteristic via its sequence specific activity.

The present invention provides a rapid, powerful, highly adaptable and yet simplified target specific screening assay for the discovery and identification of inhibitors and activators of the RNA template-directed nucleic acid polymerases, which includes the RNA-dependent DNA polymerases (reverse transcriptases) and the RNA-dependent RNA polymerases and the DNA template-directed polymerases, which includes the DNA-dependent DNA polymerases and the DNA-dependent RNA polymerases. The essential feature of the invention is the incorporation of a functional polymerase binding site sequence (PBS) into a nucleic acid molecule which confers a discernible characteristic (for example via its sequence specific activity) such that the incorporation of the PBS renders the nucleic acid molecule a functional template for a given RNA or DNA template-directed nucleic acid polymerase. In the presence of the polymerase and primer, catalytic extension of the strand of nucleic acids complementary to the template occurs, resulting in the partial or total elimination of the characteristic-conferring activity of the reporter-template molecule described due to the antisense effects of the complementary strand (or other polymerase-mediated effects). Candidate inhibitors and activators of polymerase function are evaluated by their ability to decrease or increase the extent of the characteristic conferred by the activity of the reporter-template molecule compared to that conferred in the control situations.

The characteristic-conferring activity of the reporter-template molecule may consist of, but is not limited to, several alternative types: 1) the reporter-template molecule is a messenger RNA (mRNA) coding for a protein which confers a discernible characteristic, 2) the reporter-template molecule is a regulatory RNA or DNA controlling the expression and/or other activity of a gene or gene product which confers a discernible characteristic, or 3) the reporter-template molecule is a catalytic RNA or DNA which confers a discernible characteristic directly. All three alternatives are suitable for cell-based embodiments of the invention while the use of a catalytic RNA or DNA is particularly well-suited for in vitro embodiments of the invention. Both cell-based and in vitro assay embodiments of the invention are useful in the large scale screening of compound libraries while the use of the cell-based embodiments is particularly well-suited for massively screening compounds which are polynucleic acids, peptides, or polypeptides since these agents can be produced within the cells themselves.

The invention also provides a novel method for controlling gene expression and, in general, the activity of any nucleic acid strand of interest.

DETAILED DESCRIPTION OF THE INVENTION

The term "polymerase binding site" (abbreviated PBS) as used herein is defined as a sequence element in a nucleic acid molecule which renders the molecule a template for a specified nucleic acid polymerase by mediating interaction between the polymerase and the nucleic acid molecule. Accordingly, primer binding sequences, promoter sequences, and origins of replication, as known to those in the field are examples of polymerase binding sites. As illustrated in Orr et al, *The Journal of Biological Chemistry,* 267, 4177–4182 (1992), with a number of polymerases, including HIV-RT, primer extension assays can be performed utilizing heterologous PBS sequences (those not normally used by a given polymerase) as long as there is sufficient complementarity between a region of the template molecule and the primer molecule used. An example is the "combined" template-primer molecule poly(rA)-oligo(dT)$_{12-18}$. Such a template sequence which is complementary to the primer in question also constitutes a polymerase binding site as defined herein.

The present invention provides methods for the identification and discovery of agents which are inhibitors and activators of RNA and DNA-dependent nucleic acid polymerases. The essential feature of the invention is the incorporation of a functional polymerase binding site sequence (PBS) into a nucleic acid molecule which is chosen for its ability to confer a discernible characteristic (for example via its sequence specific activity) such that the incorporation of the PBS renders the nucleic acid molecule a functional template for utilization by a predetermined RNA or DNA template-directed nucleic acid polymerase. In the presence of the polymerase, suitable primer molecules, and any necessary accessory molecules, catalytic extension of the strand of nucleic acids complementary to the template occurs, resulting in a partial or total elimination of (or increase in) the characteristic conferring activity of the reporter-template molecule described due to the antisense effects of the complementary strand or other polymerase-mediated effects. Candidate inhibitors and activators are evaluated for their specific effects on polymerase function, versus polymerase-unrelated effects on reporter-template function, by comparing their ability to decrease or increase the extent of the reporter activity of the reporter-template molecule in the assay to their ability to do so in the control situation in which the activity of the polymerase has been eliminated from the assay.

Embodiments Related to RNA-dependent Nucleic Acid Polymerases:

FIG. 1. illustrates a single PBS incorporated into an RNA reporter strand thus forming an RNA reporter strand which is also a functional template for a given RNA-dependent nucleic acid polymerase. PBS sequences may also be multiply incorporated into the RNA reporter strand so long as such incorporation in itself does not substantially interfere with the reporter activity of the RNA strand. The incorporation of a PBS sequence or sequences into the RNA reporter strand is most easily achieved by the ligation of double stranded DNA restriction enzyme fragments containing the PBS sequence into appropriate restriction sites of a double stranded DNA molecule which is a template for the transcription of an RNA reporter strand by a DNA-dependent RNA polymerase. Alternatively the incorporation of the PBS sequence can be achieved through site-directed mutagenesis of such a DNA molecule, the total chemical synthesis of the novel RNA reporter molecule (by, for example, the phosphoramidite method using an Applied Biosystems Model 392 DNA/RNA Synthesizer), or by any other method known in the field.

The reporter activity of the reporter-template RNA molecule may consist of, but is not limited to, several preferred types.

In case 1, the RNA is a messenger RNA (mRNA) coding for a protein which confers a discernible characteristic. In this case the preferable form of the assay is cell-based such that the reporter-template RNA is produced within a suitable host cell along with the components necessary for the extension of the nucleic acid strand complementary to the reporter-template molecule, specifically the appropriate RNA-dependent nucleic acid polymerase and its necessary primer molecule if any. The characteristic-conferring protein may be, but is not limited to, an enzyme catalyzing a color reaction such as beta-galactosidase (catalyzes the chromogenic conversion of the substrate 5-bromo-4-chloro-3-indolyl-beta-D-galactoside), an enzyme conferring antibiotic resistance, such as beta-lactamase which confers resistance to ampicillin, or an enzyme conferring the metabolic complementation of an auxotrophic state.

Figure 2A:
FIGS. 2A to 2C illustrate alternative positions for the incorporation of a PBS into a messenger RNA (mRNA) molecule with respect to the positions of the start codon, denoted AUG, and the stop codon, denoted UAG, of the mRNA molecule.
Figure 2B:
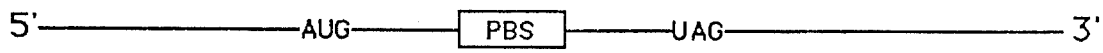
Figure 2C:

FIG.'s 2A–C illustrate the alternative positions for the incorporation of a PBS into an mRNA molecule with respect to the positions of the start codon and stop codon of the mRNA molecule. FIG. 2A illustrates the incorporation of a PBS into the 3' non-coding sequence of the mRNA. FIG. 2B illustrates the incorporation of the PBS into the protein coding sequence of the mRNA. Incorporation of the PBS into this region is appropriate as long it does not change the coding sequence such that a non-functional characteristic-conferring protein is produced. FIG. 2C illustrates the incorporation of a PBS into the 5' non-coding region of the mRNA. This region contains the ribosome binding site and other regulatory sequences. Polymerase activity initiated by binding at the PBS in any of these regions can prevent translation of the mRNA by at least one of several mechanisms such as a direct block of sense strand translation by the complementary strand, the complementary strand-facilitated degradation and/or modification of the sense strand by enzymes such as RNAse H (degrades RNA:DNA duplexes) and E. coli RNAse III (degrades RNA:RNA duplexes), interference with the RBS by formation of its complementary strand and/or its degradation. Binding of the polymerase to its PBS without the ensuing synthesis of the complementary strand may also prevent translation due to steric interference with the translational apparatus, in particular this may be expected to occur if the PBS sequence is located near the RBS or between the RBS and the end of the protein coding sequence, but not in the 3' non-coding region or necessarily at other sites 5' to the RBS in the 5' non-coding region. The choice of PBS incorporation sites will be partly influenced by the need or lack of need to specifically determine the differential effects agents have on polymerase/PBS binding and on complementary strand extension by the polymerase. The invention is not limited by the use of single or multiple PBS sequences incorporated into one or more of the alternate positions described in the same mRNA molecule.

In case 2, the reporter-template RNA molecule is a regulatory RNA controlling the expression and/or other activity of one or more genes or gene products which confer a discernible characteristic. In this case also, the components of the assay are preferably produced within a suitable host cell as part of a cell-based assay.

In case 3, the reporter-template RNA molecule is a catalytic RNA molecule which confers a discernible characteristic directly, by virtue of its catalytic activity. This activity may include, but is not limited to the catalysis of color reactions. This embodiment of the invention is particularly suited for use in conducting large scale microtiter plate type in vitro assays because of the limited number of components required, the ability to perform an assay from start to finish in one reaction chamber with no washing steps, and the ability to directly determine the results colorimetrically. In one version of the assay, all that is required is a suitable reaction buffer for function of both the RNA-dependent nucleic acid polymerase in question and the catalytic reporter-template RNA molecule (this buffer should contain the required nucleic acid monomers, the color substrate, the polymerase primer if any, and any necessary accessory molecules), the polymerase, and the reporter-template. If the RNA-dependent polymerase in question requires a polynucleic acid primer, such as that required by HIV-RT, this requirement may be satisfied by inclusion of the primer in the reaction buffer or by incorporation of the primer sequence into the 3' sequence of the catalytic reporter-template RNA molecule itself. Integral incorporation of the primer as described is not limited to this embodiment of the invention. The catalytic reporter-template RNA molecule described may also be an RNA:DNA hybrid in which the incorporated primer and perhaps some other sequence of the molecule is composed wholly or partly of deoxyribonucleic acids.

Embodiment Related to DNA-dependent DNA Polymerases:

In this embodiment the reporter-template molecule is preferably a catalytic DNA molecule which confers a discernible characteristic directly, by virtue of its catalytic activity. This embodiment is analogous to that for RNA-dependent nucleic acid polymerases in which the reporter-template is a catalytic RNA. Functional interaction of a DNA-dependent DNA polymerase and the reporter-template reduces the catalytic activity of the reporter-template and provides an assay for inhibitors and activators of polymerase activity as previously described.

Embodiment Related to DNA-dependent RNA Polymerases:

In this embodiment the reporter-template is a single stranded, partially double stranded, or double stranded DNA molecule which confers a discernible characteristic, preferably in a direct manner via sequence specific catalytic activity. Such a reporter-template contains the promoter sequence and other sequences necessary to direct transcription of RNA. Functional interaction of a DNA-dependent RNA polymerase and the reporter-template reduces the latter's catalytic activity and provides an assay for inhibitors and activators of polymerase activity as previously described.

Embodiment Related to a Method for Controlling the Activity of a Nucleic Acid Molecule:

In this embodiment, the invention is used to control gene expression and, in general, the activity of any nucleic acid strand of interest. By operably linking the activity of a predetermined nucleic acid polymerase to a nucleic acid strand of interest-(as described above), the expression of, or other activity of, the nucleic acid strand can be controlled by the addition and subtraction of the polymerase itself, cofactors of the polymerase, or inhibitors and activators of the polymerase in question. In a preferred version, the cellular expression of a specified protein is controlled by operably linking the activity of an RNA-dependent nucleic acid polymerase to an mRNA molecule coding for the protein. When both articles are present with necessary cofactors in the cell, translation is diminished as a result of the action of the polymerase on the mRNA. Inhibitors of the polymerase may, therefore, be used to induce translation of the mRNA. Alternatively, repression of the polymerase itself can be used to achieve the same result, while induction of the polymerase can be used to diminish translation of the message.

Ramifications:

Both the cell-based assay and in vitro assay embodiments of the invention may be used for the screening of candidate inhibitors and activators of RNA and DNA-dependent nucleic acid polymerases. The cell-based embodiments of the invention may utilize any suitable host cell as long as the components of the assay are functional in the cell type in question. These host cell types may include but are not limited to mammalian cells, yeasts and bacteria. Cells engineered to embody the invention in its test and control formats may be referred to here as assay cells and control cells, respectively. The ability to perform the assay with clinically relevant cell types is an advantage in predicting the actual therapeutic value of agents. The ability to perform the assay using well-characterized microbiological hosts such as yeasts and bacteria is an advantage in that the technology for the propagation and manipulation of these organisms is well established. The cell-based embodiments of the invention are particularly suited for screening compounds which can be produced by the host cells themselves such as but not limited to RNA molecules, peptides, and proteins. In a preferred embodiment of the invention bacterial assay cells are first transformed with a combinatorial vector library in which the vector DNA contains elements which direct the production of cellular products and then plated out on an appropriate selective media for determining the extent of the reporter activity expressed by the reporter-template molecule in the cells of the resulting colonies. Colonies resulting from cells which produce inhibitors or activators of the particular RNA or DNA-dependent nucleic acid polymerase in the assay are thus selected by determining the extent of the characteristic conferred by the reporter-template molecule. These cells can then be propagated and the particular vector DNA coding for the putative inhibitor or activator can be isolated and analyzed. The cell-based embodiments of the invention can also be used for the discovery of inhibitors and activators which indirectly affect RNA and DNA-dependent polymerase function via modulation of endogenous cellular biological pathways (whether such pathways in question are known or not). The cell-based embodiments of the invention are also particularly suited for the identification of non-chemical treatments which inhibit or activate polymerase function directly or indirectly. Such treatment may include, but is not limited to, exposure to radiation and variation of physical conditions.

RNA-degrading and/or modifying enzymes which may be used in the assay as described may be endogenous to the host cells, introduced by genetic methods to the host cells, or directly provided to the assay in the case of in vitro embodiments of the invention. Given a particular inhibitor or activator, the invention can be used to identify agents which agonize or antagonize its effects on RNA or DNA-dependent nucleic acid polymerase function by performing the described assays in the presence of the particular effector and the agents to be screened.

The invention is not limited by the means of incorporation of a PBS sequence into a template. In addition to those described, these means may also include the generation of a heterologous PBS by providing a primer sequence sufficiently complementary to a region of the reporter-template without any modification of the template itself. The invention is not limited by the singularity, multiplicity, or position of PBS sequences incorporated into the reporter-template structure nor is the invention limited by the nature of the discernible characteristic conferred by the reporter-template molecule. The invention is not limited by the means of production of its components, the means of introduction and incorporation of these components into cells, nor the nature and means of introduction of agents to be tested by the assays provided by the invention. The invention is not limited by the order of addition of its components and the agents to be tested. Further, with respect to the cell-based embodiments, the invention is not limited by the subcellular compartment in which its components are processed and ultimately function. It is to be understood that the above descriptions are meant to be illustrative and not limiting. Many embodiments will be apparent to those of skill in the art upon reviewing the above descriptions. The scope of the invention should, therefore, be determined not with reference to the above descriptions, but should instead be determined with reference to the appended claims, along with the full scope of equivalents to which such claims are entitled.

What is claimed is:

1. A polynucleic acid reporter-template molecule comprising:
    a) means for conferring at least one discernable characteristic and
    b) rendering means for rendering said nucleic acid molecule a functional template for at least one predetermined nucleic acid polymerase so that utilization of said polynucleic acid molecule as a template by said polymerase causes a discernable change in the extent of the characteristic conferring activity of said polynucleic acid molecule.

2. The polynucleic acid molecule of claim 1 wherein said rendering means renders said nucleic acid molecule a functional template for at least one predetermined nucleic acid polymerase so that utilization of said polynucleic acid molecule as a template by said polymerase discernably diminishes the extent of the characteristic conferring activity of said polynucleic acid molecule.

3. The polynucleic acid molecule of claim 1 wherein said rendering means renders said nucleic acid molecule a functional template for at least one predetermined nucleic acid polymerase so that utilization of said polynucleic acid molecule as a template by said polymerase discernably increases the extent of the characteristic conferring activity of said polynucleic acid molecule.

4. The polynucleic acid molecule of claim 1 wherein said means for conferring at least one discernable characteristic exclusively confers discernable characteristics other than the ability to render said polynucleic acid molecule a template of a template directed nucleic acid polymerase and other than the ability to direct the transcription of an mRNA molecule which codes for a protein which confers a discernable characteristic.

5. The polynucleic acid molecule of claim 1 wherein said polynucleic acid molecule is substantially composed of ribonucleic acids and said polymerase is a RNA dependent nucleic acid polymerase.

6. The polynucleic acid molecule of claim 1 wherein said polynucleic acid molecule is substantially composed of deoxyribonucleic acids and said polymerase is a DNA dependent nucleic acid polymerase.

7. The polynucleic acid molecule of claim 1 wherein said polynucleic acid molecule contains an integral polymerase binding site for said polymerase.

8. The polynucleic acid molecule of claim 1 wherein said polynucleic acid molecule contains an integral primer binding site for said polymerase.

9. The polynucleic acid molecule of claim 1 wherein said polynucleic acid molecule contains an integral primer and integral primer binding site for said polymerase.

10. The polynucleic acid molecule of claim 1 wherein said means for conferring at least one discernable characteristic confers cellular resistance to a predetermined antibiotic.

11. The polynucleic acid molecule of claim 1 wherein said means for conferring at least one discernable characteristic confers the ability to complement auxotrophy in auxotrophic cells growing on minimal media.

12. The polynucleic acid molecule of claim 1 wherein said means for conferring at least one discernable characteristic confers the ability to colorimetrically transform a chromogenic substrate.

13. The polynucleic acid molecule of claim 11 wherein said means for conferring at least one discernable characteristic is at least one integral catalytic nucleic acid sequence conferring at least one discernable characteristic.

14. The polynucleic acid molecule of claim 1 wherein said means for conferring a discernable characteristic is at least one integral protein coding nucleic acid sequence conferring at least one discernable characteristic.

15. The polynucleic acid molecule of claim 1 wherein said means for conferring a discernable characteristic is at least one integral regulatory nucleic acid sequence conferring at least one discernable characteristic.

16. A method of screening for inhibitors and activators of a predetermined nucleic acid dependent nucleic acid polymerase comprising the steps of:
  a) associating a polynucleic acid molecule comprising:
    i) means for conferring at least one discernable characteristic and
    ii) rendering means for rendering said nucleic acid molecule a functional template for said polymerase so that utilization of said polynucleic acid molecule as a template by said polymerase causes a discernable change in the extent of the characteristic conferring activity of said polynucleic acid molecule,
  with said polymerase into an operably linked test assemblage
  b) applying candidate inhibitors and activators of said polymerase to said test assemblage
  c) applying said candidate inhibitors and activators to a control assemblage comprising means for quantifying the change caused in the characteristic conferring activity of said nucleic acid molecule by said candidate inhibitors and activators which is not the result of inhibition or activation of said polymerase
  d) determining if said candidate inhibitors and activators affect the activity of said polymerase by comparing the effect caused by said candidate inhibitors and activators on the conferring of the discernable characteristic by the nucleic acid molecule of the test assemblage of step a) to the effect caused by the same candidate inhibitors and activators on the control assemblage of step c).

17. A method according to claim 16 wherein the control assemblage of step c) comprises the polynucleic acid molecule of claim 16 step a) not functionally associated with a template directed nucleic acid polymerase.

18. A method according to claim 16 wherein said means for conferring a discernable characteristic is at least one integral catalytic nucleic acid sequence conferring at least one discernable characteristic.

19. A method according to claim 16 wherein said means for conferring a discernable characteristic is at least one integral protein coding nucleic acid sequence conferring at least one discernable characteristic.

20. A method according to claim 16 wherein said means for conferring a discernable characteristic is at least one integral regulatory nucleic acid sequence conferring at least one discernable characteristic.

21. A method for controlling the activity of a polynucleic acid molecule comprising the steps of:
  a) rendering said polynucleic acid molecule a template for the template directed polymerization of nucleic acids by at least one preselected nucleic acid dependent nucleic acid polymerase whereby said template directed polymerization diminishes or increases the activity of said molecule
  b) regulating the amount of functional interaction between said molecule and said polymerase.

22. A method according to claim 21 wherein step b) comprises regulating the amount of functional interaction between said polynucleic acid molecule and said polymerase by controlling the activity of said polymerase by using effectors selected from the group consisting of inhibitors and activators of said polymerase.

23. A method according to claim 21 wherein step b) comprises regulating the amount of functional interaction between said polynucleic acid molecule and said polymerase by controlling the amount of said polymerase available to utilize said polynucleic acid molecule as a template.

24. A method according to claim 21 wherein said polynucleic acid molecule is a messenger RNA molecule.

25. A method according to claim 21 wherein said polynucleic acid molecule is a catalytic polynucleic acid molecule.

26. A method according to claim 21 wherein said polynucleic acid molecule is a regulatory polynucleic acid molecule.

* * * * *